United States Patent [19]
Dyllick-Brenzinger et al.

[11] Patent Number: 5,627,077
[45] Date of Patent: May 6, 1997

[54] ANILINES AS MARKERS FOR MINERAL OILS

[75] Inventors: Rainer Dyllick-Brenzinger, Weinheim, Germany; Friedrich-Wilhelm Raulfs, Kobe, Japan; Ulrike Schlösser, Ludwigshafen, Germany

[73] Assignee: BASF Aktiengesellschaft, Ludwigshafen, Germany

[21] Appl. No.: 424,497

[22] PCT Filed: Nov. 9, 1993

[86] PCT No.: PCT/EP93/03133

§ 371 Date: Jun. 22, 1995

§ 102(e) Date: Jun. 22, 1995

[87] PCT Pub. No.: WO94/11466

PCT Pub. Date: May 26, 1994

[30] Foreign Application Priority Data

Nov. 19, 1992 [DE] Germany .................. 42 38 994.1

[51] Int. Cl.$^6$ .................. G01N 33/00; G01N 37/00
[52] U.S. Cl. .................. 436/106; 436/56; 436/60; 436/164; 436/169; 436/178; 534/558; 534/573; 44/328
[58] Field of Search .................. 436/56, 60, 106, 436/164, 166, 169, 178; 44/328; 534/558, 573

[56] References Cited

U.S. PATENT DOCUMENTS

| | | | |
|---|---|---|---|
| 2,689,171 | 9/1954 | Hager et al. | 436/56 |
| 4,209,302 | 6/1980 | Orelup | 44/59 |
| 5,252,106 | 10/1993 | Hallisy | 44/328 |
| 5,266,227 | 11/1993 | Reichelt et al. | 44/328 X |

OTHER PUBLICATIONS

CRC Handbook of Chemistry and Physics, 65th Edition, 1984–1985, pp. D–148, D–149 and D–150.

*Primary Examiner*—Jill Warden
*Assistant Examiner*—Maureen M. Wallenhorst
*Attorney, Agent, or Firm*—Oblon, Spivak, McClelland, Maier & Neustadt, P.C.

[57] ABSTRACT

Anilines of the formula

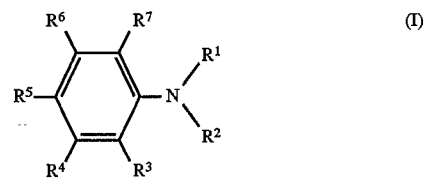

where
$R^1$ and $R^2$ are each hydrogen, unsubstituted or substituted alkyl, alkenyl or unsubstituted or substituted phenyl or $R^1$ and $R^2$, together with the nitrogen atom linking them are a heterocyclic radical or $R^1$ may furthermore be unsubstituted or substituted hydroxyl or unsubstituted or substituted amino, $R^3$ and $R^7$ are each hydrogen, unsubstituted or substituted alkyl, alkenyl, cyano, nitro, acyl, acylamino, unsubstituted or substituted hydroxyl, unsubstituted or substituted carboxymethyl, unsubstituted or substituted amino, unsubstituted or substituted mercapto or unsubstituted or substituted sulfamoyl or, together with $R^2$, are alkylene, alkenylene or phenylalkenylene, $R^4$ is hydrogen, unsubstituted or substituted alkyl, alkenyl, unsubstituted or substituted hydroxyl, unsubstituted or substituted amino, unsubstituted or substituted carboxyl or unsubstituted or substituted sulfamoyl and $R^5$ and $R^6$ are each hydrogen, unsubstituted or substituted alkyl, alkenyl, unsubstituted or substituted phenyl, nitro, acylamino, unsubstituted or substituted hydroxyl, unsubstituted or substituted amino, unsubstituted or substituted sulfamoyl, alkyl-, alkenyl- or arylsulfonyl, acyl or unsubstituted or substituted carboxyl, with the proviso that at least one of the radicals $R^3$, $R^5$ or $R^7$ is hydrogen,
are used for marking mineral oils, and the above-mentioned anilines are detected in mineral oils.

9 Claims, No Drawings

ANILINES AS MARKERS FOR MINERAL OILS

BRIEF SUMMARY OF THE INVENTION

The present invention relates to the use of anilines of the formula I

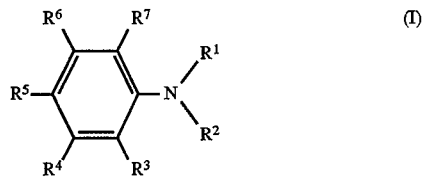

where
- $R^1$ and $R^2$ independently of one another are each hydrogen, $C_1$–$C_{18}$-alkyl which is unsubstituted or substituted and may be interrupted by 1 to 3 oxygen atoms as ether functional groups or from 1 to 3 $C_1$–$C_4$-alkylimino groups, or $C_3$–$C_{18}$-alkenyl or unsubstituted or substituted phenyl, or $R^1$ and $R^2$ together with the nitrogen atom which links them, may be a 5-membered or 6-membered saturated heterocyclic radical which may have a further hetero atom, or $R^1$ may furthermore be a radical of the formula $OL^1$ or $NL^1L^2$, where $L^1$ and $L^2$ independently of one another are each hydrogen, unsubstituted or substituted $C_1$–$C_{18}$-alkyl, $C_3$–$C_{18}$-alkenyl or unsubstituted or substituted phenyl,
- $R^3$ and $R^7$ independently of one another are each hydrogen, unsubstituted or substituted $C_1$–$C_{18}$-alkyl, $C_2$–$C_{18}$-alkenyl, cyano, nitro, formyl, unsubstituted or substituted $C_2$–$C_4$-alkanoyl, formylamino, unsubstituted or substituted $C_2$–$C_4$-alkanoylamino, benzoylamino or a radical of the formula $OL^1$, $CH_2COOL^1$, $NL^1L^1$, $SL^1$ or $SO_2NL^1L^2$, where $L^1$ and $L^2$ each have the abovementioned meanings, or together with $R^2$ are $C_2$- or $C_3$-alkylene which is unsubstituted or monosubstituted to trisubstituted by methyl or are unsubstituted or phenyl-substituted $C_2$- or $C_3$-alkenylene,
- $R^4$ is hydrogen, unsubstituted or substituted $C_1$–$C_{18}$-alkyl, $C_2$–$C_{18}$-alkenyl, nitro or a radical of the formula $OL^1$, $NL^1L^2$, $COOL^1$ or $SO_2L^1L^2$, where $L^1$ and $L^2$ each have the abovementioned meanings, and
- $R^5$ and $R^6$ independently of one another are each hydrogen, unsubstituted or substituted $C_1$–$C_{18}$-alkyl, $C_2$–$C_{18}$-alkenyl, unsubstituted or substituted phenyl, nitro, formylamino, unsubstituted or substituted $C_2$–$C_4$-alkanoylamino, benzoylamino or a radical of the formula $OL^1$, $NL^1L^2$, $SO_2NL^1L^2$, $SO_2L^3$, $COL^1$ or $COOL^1$, where $L^1$ and $L^2$ each have the abovementioned meanings and $L^3$ is unsubstituted or substituted $C_2$–$C_{18}$-alkyl, $C_3$–$C_{18}$-alkenyl or unsubstituted or substituted phenyl, with the proviso that at least one of the radicals $R^3$, $R^5$ or $R^7$ is hydrogen, for marking mineral oils, the anilines of the formula I, during their detection as the marker, being coupled to a diazonium salt, with formation of an azo dye, mineral oils marked with the abovementioned anilines and to a method for detecting the abovementioned anilines in mineral oils.

BACKGROUND OF THE INVENTION

U.S. Pat. No. 4 209 302 discloses the use of α- or β-naphthylamine which carries, on the amino group, a propyl radical substituted by a further amino group for marking mineral oils. The marker is detected by reacting the naphthylamine with diazotized 2-chloro-4-nitroaniline. However, it has been found that this marking and detection method is not yet completely satisfactory.

Furthermore, U.S. Pat. No. 2,689,171 describes the marking of mineral oils with aniline or p-toluidine, these products being used as diazo components for the formation of azo dyes; i.e. during their detection they are diazotized and coupled with a coupling component, for example β-naphthol.

OBJECTS OF THE INVENTION

It is an object of the present invention to provide novel agents for marking mineral oils. The novel agents should be easily obtainable and readily soluble in mineral oils. Moreover, they should be capable of being detected in a simple manner. It should also be possible for even very small amounts of marker to be rendered visible by a strong color reaction. Finally, the marker should not be capable of being removed from the marked mineral oil by simple extraction with water.

DETAILED DESCRIPTION OF THE PREFERRED EMBODIMENTS

We have found that this object is achieved and that the anilines of the formula I which are defined at the outset could be advantageously used for marking mineral oils.

All alkyl and alkenyl radicals occurring in the abovementioned formula I may be both straight-chain and branched.

For the purposes of the present invention, alkenyl radicals must be understood as being essentially radicals which have 1 to 3 double bonds.

If substituted alkyl groups occur in the above-mentioned formula I, suitable substituents are, for example, hydroxyl, $C_1$–$C_4$-alkoxy, phenoxy, cyano, phenyl, $C_1$–$C_4$-dialkylamino, $C_1$–$C_4$-alkanoyloxy, 1-$C_1$–$C_4$-alkoxy-$C_2$–$C_4$-alkoxy, N—$C_1$–$C_4$-alkyl-N-hydroxy-$C_2$–$C_4$-alkylcarbamoyl, $C_1$–$C_4$-alkoxycarbonyl, phenoxycarbonyloxy, $C_1$–$C_4$-alkylaminocarbonyloxy, phenylaminocarbonyloxy or acetacetoxy. The alkyl groups have, as a rule, 1 or 2 substituents.

If substituted phenyl groups occur in the above-mentioned formula I, suitable substituents are, for example, $C_1$–$C_4$-alkyl or $C_1$–$C_4$-alkoxy. The phenyl groups have, as a rule, from 1 to 3 substituents.

If $R^1$ and $R^2$, together with the nitrogen atom linking them, are a 5-membered or 6-membered saturated heterocyclic radical which may have a further hetero atom, examples of suitable radicals for this purpose are pyrrolidinyl, piperidinyl, morpholinyl, piperazinyl or N—$C_1$–$C_4$-alkylpiperazinyl.

$R^1, R^2, R^3, R^4, R^5, R^6, R^7, L^1, L^2$ and $L^3$ are, for example, methyl, ethyl, propyl, isopropyl, butyl, isobutyl, sec-butyl, pentyl, isopentyl, neopentyl, tertpentyl, hexyl, 2-methylpentyl, heptyl, octyl, 2-ethylhexyl, isooctyl, nonyl, isononyl, decyl, isodecyl, undecyl, dodecyl, tridecyl, 3,5,5,7-tetramethylnonyl, isotridecyl, (the above names isooctyl, isononyl, isodecyl and isotridecyl are trivial names and originate from the alcohols obtained by the oxo synthesis; cf. Ullmanns Encyklopädie der technischen Chemie, 4th Edition, Volume 7, pages 215 to 217, and Volume 11, pages 435 and 436), tetradecyl, pentadecyl, hexadecyl, heptadecyl, octadecyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 2- or 4-butoxybutyl, cyanomethyl, 2-cyanoethyl, 3-cyanopropyl, 2-cyanobutyl, 4-cyanobutyl, 5-cyanopentyl, 6-cyanohexyl, 2-hydroxyethyl, 2-hydroxypropyl, 3-hydroxypropyl, 2-hydroxybutyl, 4-hydroxybutyl, 5-hydroxypentyl, 6-hydroxyhexyl, 5-hydroxy-3-oxapentyl, benzyl, 1-phenylethyl, 2-phenylethyl, 2-formyloxyethyl, 2-acetoxyethyl, 2-propionyloxyethyl, 2-isobutyryloxyethyl, 2- or 3-formyloxypropyl, 2- or 3-acetoxypropyl, 2- or 3-propionylpropyl, 2- or 3-isobutyryloxypropyl, 2- or 4-formyloxybutyl, 2- or 4-acetyloxybutyl, 2- or 4-propionyloxybutyl, 2- or 4-isobutyryloxybutyl, N-methyl-N-(2-hydroxyethyl)-carbamoyl, 2-methoxycarbonylethyl, 2-ethoxycarbonylethyl, 2-phenoxycarbonyloxyethyl, 2-methylaminocarbonyloxyethyl, 2-ethylaminocarbonyloxyethyl, 2-isopropylaminocarbonyloxyethyl, 2-phenylaminocarbonyloxyethyl, 2-acetacetoxyethyl, allyl prop-1-en-1-yl, methallyl, ethallyl, pentenyl, pentadienyl, hexadienyl, 3,7-dimethylocat-1,6-dien-1-yl, undec-10-en-1-yl, 6,10-dimethylundeca-5,9-dien-2-yl, 3,7,11-trimethyldodeca-1,6,10-trien-1-yl, 3,7,11-trimethyldodeca-2,6,10-trien-1-yl, octadec-9-en-1-yl, octadeca-9,12-dien-1-yl, octadeca-9,12,15-trien-1-yl, 6,10,14-trimethylpentadeca-5,9,13-trien-2-yl, hydroxy, methoxy, ethoxy, propoxy, isopropoxy, butoxy, isobutoxy, sec-butoxy, pentyloxy, isopentyloxy, neopentyloxy, tertpentyloxy, hexyloxy, heptyloxy, octyloxy, isooctyloxy, 2-ethylhexyloxy, nonyloxy, isononyloxy, decyloxy, isodecyloxy, undecyloxy, dodecyloxy, tridecyloxy, isotridecyloxy, tetradecyloxy, pentadecyloxy, hexadecyloxy, heptadecyloxy, octadecyloxy, amino, mono- or dimethylamino, mono- or diethylamino, mono- or dipropylamino, mono- or diisopropylamino, mono- or dibutylamino, N-methyl-N-ethylamino, mono- or diallylamino, phenylamino or N-phenyl-N-methylamino.

$R^1$ and $R^2$ are furthermore, for example, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 4,8-dioxadecyl, 3,6,8-trioxadecyl, 3,6,9-trioxaundecyl, 2-dimethylaminoethyl, 2-diethylaminoethyl, 2- or 3-dimethylaminopropyl, 2- or 3-diethylaminopropyl, 2- or 4-dimethylaminopropyl, 2- or 4-diethylaminobutyl, 3,6-dimethyl-3,6-diazaheptyl, 3,6,9-trimethyl-3,6,9-triazadecyl, 2-(1-methoxyethoxy)ethyl, 2-(1-ethoxyethoxy)ethyl, 2-(1-isobutoxyethoxy)ethyl, 2- or 3-(1-methoxyethoxy)propyl, 2- or 3-(1-ethoxyethoxy)propyl or 2- or 3-(1-isobutoxyethoxy) propyl.

$R^1$, $R^2$, $R^5$ and $R^6$ are furthermore, for example, phenyl, 2-, 3- or 4-methylphenyl, 2-, 3- or 4-ethylphenyl, 2,4-dimethylphenyl, 2-, 3- or 4-methoxyphenyl, 2-, 3- or 4-ethoxyphenyl or 2,4-dimethoxyphenyl.

$R^3$, $R^5$, $R^6$ and $R^7$ are furthermore, for example, formylamino, acetylamino, propionylamino, butyrylamino or isobutyrylamino.

$R^3$, $R^4$, $R^5$, $R^6$ and $R^7$ are furthermore, for example, vinyl, sulfamoyl, mono- or dimethylsulfamoyl, mono- or diethylsulfamoyl, mono- or dipropylsulfamoyl, mono- or diisopropylsulfamoyl, mono- or dibutylsulfamoyl, N-methyl-N-ethylsulfamoyl, mono- or diallylsulfamoyl or phenylsulfamoyl.

$R^3$ and $R^7$ are furthermore, for example, carboxymethyl, methoxycarbonylmethyl, ethoxycarbonylmethyl, propoxycarbonylmethyl, isopropoxycarbonylmethyl, butoxycarbonylmethyl, allyloxycarbonylmethyl, phenoxycarbonylmethyl, mercapo, methylthio, ethylthio, propylthio, isopropylthio or butylthio.

$R^4$, $R^5$ and $R^6$ are furthermore, for example, carboxyl, methoxycarbonyl, ethoxycarbonyl, propoxycarbonyl, isopropoxycarbonyl, butoxycarbonyl, allyloxycarbonyl, phenoxycarbonyl, allylthio or phenylthio.

$R^5$ and $R^6$ are furthermore, for example, methylsulfonyl, ethylsulfonyl, propylsulfonyl, isopropylsulfonyl, butylsulfonyl, phenylsulfonyl, formyl, acetyl, propionyl, butyryl, isobutyryl or benzoyl.

$R^2$ and $R^3$ or $R^2$ and $R^7$ together are, for example, 1,3-propylene, 1,1,3-trimethyl-1,3-propylene, vinylene, phenylvinylene or a radical of the formula CH=CH—CH$_2$.

Preferred anilines of the formula I, where $R^1$ and $R^2$ independently of one another are each hydrogen, $C_1$–$C_{15}$-alkyl which is unsubstituted or substituted and may be interrupted by 1 to 3 oxygen atoms in the ether function or from 1 to 3 $C_1$–$C_4$-alkylimino groups, or allyl or unsubstituted or substituted phenyl, or $R^1$ and $R^2$, together with the nitrogen atom which links them, are a 5-membered or 6-membered saturated heterocyclic radical which may have a further hetero atom, $R^3$ and $R^7$ independently of one another are each hydrogen or $C_1$–$C_4$-alkoxy or, together with $R^2$, are 1,3-propylene which is unsubstituted or monosubstituted to trisubstituted by methyl, $R^4$ and $R^5$ are each hydrogen and $R^6$ is hydrogen, $C_1$–$C_4$-alkyl, $C_1$–$C_4$-alkoxy, $C_1$–$C_4$-alkanoylamino or benzoylamino, are preferably used for marking mineral oils.

Anilines of the formula I, where $R^1$ and $R^2$ are each hydrogen or $C_1$–$C_4$-alkyl or at least one of the two radicals $R^1$ and $R^2$ is $C_2$–$C_{15}$-alkyl which is substituted by hydroxyl and may be interrupted by from 1 to 3 oxygen atoms in the ether function or from 1 to 3 $C_1$–$C_4$-alkylamino groups and $R^6$ is $C_1$–$C_4$-alkyl, in particular methyl, are particularly preferably used for marking mineral oils.

Anilines of the formula I where $R^3$ is hydrogen, $C_1$–$C_4$-alkyl, $C_1$–$C_4$-alkoxy and $R^6$ is hydrogen, $C_1$–$C_4$-alkyl, $C_1$–$C_4$-alkoxy, amino or acetylamino are also particularly preferably used for marking mineral oils.

Anilines of the formula I where $R^7$ is hydrogen, $C_1$–$C_4$-alkyl or $C_1$–$C_4$-alkoxy are also particularly preferably used for marking mineral oils.

In particular, anilines of the formula I where at least one of the two radicals $R^1$ and $R^2$ is $C_2$–$C_4$-alkyl which is substituted by hydroxyl and $R^6$ is methyl are used for marking the mineral oils.

The use of anilines of the formula I where $R^1$ and $R^2$ are each $C_2$–$C_4$-alkyl which is substituted by hydroxyl, in particular 2-hydroxyethyl or 2- or 3-hydroxypropyl, or $R^1$ is $C_2$–$C_4$-alkyl which is substituted by hydroxyl, in particular 2-hydroxyethyl or 2- or 3-hydroxypropyl and $R^2$ is $C_1$–$C_4$-alkyl, for marking mineral oils is noteworthy.

The use of 2-methoxy- or 2-ethoxy-5-acetylaminoaniline for marking mineral oils is also noteworthy.

The present invention furthermore relates to mineral oils containing one or more of the anilines of the formula I, aniline and p-toluidine being excluded.

For the purposes of the present invention, mineral oils are to be understood as being, for example, fuels, such as gasoline, kerosene or diesel oil, or oils, such as fuel oil or engine oil.

The anilines of the formula I are particularly suitable for marking mineral oils for which an identification is required, for example for tax reasons. To minimize the costs of the identification, it is desirable to use very small amounts of marker.

For the marking of mineral oils, the anilines of the formula I are used either in the absence of a solvent or in the form of solutions. Preferred solvents are aromatic hydrocarbons, such as dodecylbenzene, diisopropylnaphthalene or a mixture of higher aromatics which is commercially available under the name Shellsol® AB (from Shell). To avoid high viscosity of the resulting solutions, a concentration of aniline I of from 30 to 50% by weight, based on the solution, is generally chosen.

By means of the anilines of the formula I which are to be used according to the invention, it is possible to detect marked mineral oils in a very simple manner even if the marking substances are present only in a concentration of about 10 ppm or less.

The anilines of the formula I which are used as markers are advantageously detected in mineral oils if the aniline of the formula I is extracted by treating the mineral oil with an aqueous medium and coupled in the aqueous phase, in the presence or absence of a buffer, with a diazonium salt which is derived from an amine from the aminoanthraquinone, aminonaphthalene, aniline, aminothiophene, aminothiazole or aminobenzoisothiazole series, with formation of an azo dye.

The anilines of the formula I which are used as markers are particularly advantageously detected in mineral oils if the aniline of the formula I is extracted by treating the mineral oil with an aqueous solution of the diazonium salt and then coupled, in the presence or absence of a buffer, with the diazonium salt, with formation of an azo dye.

Suitable acids on which the acidic aqueous solutions are based are, for example, inorganic or organic acids, such as hydrochloric acid, sulfuric acid, nitric acid, phosphoric acid, formic acid, acetic acid or propionic acid. The acidic aqueous solutions generally have an acid concentration of from 0.5 to 20% by weight.

The anilines of the formula I which are used as markers are furthermore particularly advantageously detected in mineral oils if the aniline of the formula I is extracted by treating the mineral oil with an aqueous medium and coupled in the aqueous phase, in the presence or absence of a buffer, with the diazonium salt which is present in the solid state on a substrate, with formation of an azo dye.

Suitable aqueous media for extracting the aniline of the formula I from the mineral oil are, for example, water or mixtures of water with acids and/or water-miscible organic solvents and/or inorganic substances.

Suitable acids are the above-mentioned acids in the stated concentrations.

Examples of water-miscible organic solvents are alcohols, such as methanol, ethanol, propanol, isopropanol, ethylglycol or 1,2-propylene glycol, ethers, such as 2-methoxyethanol, 2-ethoxyethanol, 2-butoxyethanol, 2-(2-methoxyethoxy)ethanol, 1-methoxypropan-2-ol or tetrahydrofuran, carboxamides, such as N,N-dimethylformamide or N-methylpyrrolidone, propylene carbonate, dimethyl sulfoxide or sulfolane. The amount of water-miscible organic solvent is in general from 1 to 50% by weight, based on the weight of the aqueous medium.

Inorganic substances are, for example, salts, such as alkali metal halides, aluminum halides or zinc halides, or ammonia.

It is preferable to use, as an aqueous medium, an aqueous acid which may furthermore contain a water-miscible organic solvent.

Suitable substrates are inorganic materials, such as active carbon, molecular sieves, kieselguhr, titanium dioxide, alumina or calcium chloride, or organic materials, such as cellulose fibers, cotton, groundwood, polystyrene or polyvinyl chloride.

After the addition of the diazonium salt present on the substrate to the aqueous extract of the aniline of the formula I, the diazonium salt is completely or partially dissolved and thus made available for the azo coupling.

In order to achieve optimum coupling reaction, which may take place in the presence of a solvent, and hence to optimize the yield of azo dye, it is advisable to control the pH by using a buffer substance and to use the reactants in an advantageous molar ratio (aniline: diazonium salt from 1:500 to 1:1, preferably from 1:100 to 1:20).

Examples of suitable buffer substances are alkali metal acetates, monoalkali metal citrates, alkali metal dihydrogen phosphates, in particular the sodium salts in each case, or buffer systems as stated in Handbook of Chemistry and Physics, 65th Ed., 1984–1985, pages D148 to 150.

The detection of the anilines of the formula I by means of a diazo paper or of a diazo film has proven advantageous. These diazo indicators are produced by impregnating a paper, for example a filter paper, or a thin layer chromatography film which is coated with, for example, cellulose, with the corresponding diazonium salt solution, the part which comes directly into contact with the aqueous extract during development being left untreated. By immersing a paper or film strip produced in this manner in the aqueous extract, it is possible to optimize the yield of azo dye in a manner similar to paper chromatography. The azo dye being formed remains at the start and is concentrated by continuously supplied aniline and is therefore readily detectable.

Particularly noteworthy amines of the anthraquinone series are 1-aminoanthraquinone and 4-chloro-1-aminoanthraquinone.

Suitable aminonaphthalenes are, for example, of the formula II

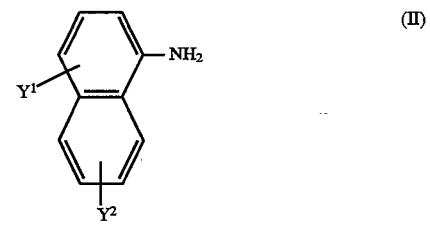

where $Y^1$ and $Y^2$ independently of one another are each hydrogen, hydroxyl or hydroxysulfonyl.

Suitable aniline on which the diazonium salts are based are, for example, of the formula III

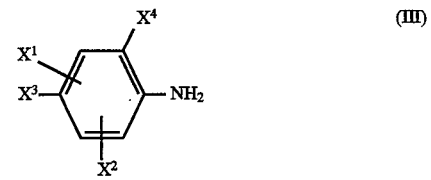

where
$X^1$ is hydrogen, halogen, $C_1$–$C_4$-alkoxy, nitro or hydroxysulfonyl, $X^2$ is hydrogen, halogen, $C_1$–$C_4$-alkoxy, cyano and nitro or is phenylazo which is unsubstituted or substituted by methyl, ethyl, methoxy or ethoxy, $X^3$ is hydrogen, $C_1$–$C_4$-dialkylamino, pyrolidino, piperidino, morpholino, nitro or hydroxysulfonyl and $X^4$ is hydrogen, halogen, cyano or a heterocyclic radical, e.g. 3-phenyl-1,2,4-oxadiazol-5-yl.

Suitable aminothiophenes, aminothiazoles or aminobenzoisothiazoles are, for example, of the formula

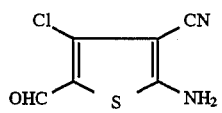

(IV)

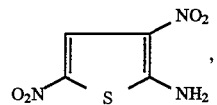

(V)

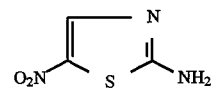

(VI)

or

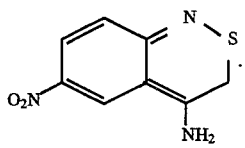

(VII)

Suitable anions which are suitable as counterions to the diazonium cations are the conventional anions, such as chloride, bromide, bisulfate, sulfate, dihydrogen phosphate, monohydrogen phosphate, phosphate, tetrafluoborate, tetrachlorozincate, naphthalene-1,5-disulfonate or acetate.

In some cases, it is advantageous also to add small amounts of alkali metal salts of arylsulfonic acids, for example the sodium salt of napthalene-1,5-disulfonic acid, as stabilizer for the diazonium salt.

A preferred detection method is one which is carried out using a diazonium salt which is derived from 1-aminoanthraquinone or from an aniline of the formula III, where $X^1$ is hydrogen, chlorine or nitro, $X^2$ is chlorine or nitro and $X^3$ is hydrogen. A detection method which is carried out using a diazonium salt which is derived from 1-aminoanthraquinone is particularly noteworthy.

As a rule, an aqueous solution of a diazonium salt which contains from 0.1 to 2% by weight, based on the weight of the solution, of diazonium salt is used for the detection reaction. In general, from 0.001 to 0.1% by weight of diazonium salt solution is used per part by weight of marked mineral oil.

As stated above, it is also possible to extract the aniline of the formula I from the mineral oil by means of an aqueous medium, in particular an aqueous acid, which may furthermore contain a water-miscible organic solvent, and to couple it with an above-mentioned diazonium salt which is present in the solid state on a substrate and is dissolved in the aqueous extract, with formation of an azo dye. The water-miscible organic solvent may be advantageous for easier transfer of the aniline I to the aqueous phase.

In this detection, it is particularly important to maintain an optimum pH. This is advantageously effected by means of a buffer substance.

A particularly suitable substrate is a paper strip, for example, of filter paper. It can be impregnated with a solution of one of the above-mentioned diazonium salts and dried. (Decomposition of the diazonium salt is prevented by storing the impregnated paper strips under dry conditions and in the dark.

If such an impregnated paper strip is immersed in the aqueous extract, a color reaction takes place at its surface owing to the formation of an azo dye. The anilines of the formula I can be detected in an extremely simple manner by this method.

In a particularly advantageous method, a few scraps of the impregnated paper strip are added to the aqueous extract and, if required, heating is carried out briefly.

The anilines of the formula I can of course also be detected in the mineral oils by means of conventional physical analytical methods, for example by gas chromatography, high pressure liquid chromatography, thin layer chromatography or column chromatography.

The anilines of the formula I which are used according to the invention as markers for mineral oils are conventional products from dye production. They are readily obtainable.

They can also be detected in very small amounts in mineral oil and give a strong color reaction during their detection.

The Examples which follow illustrate the invention.

EXAMPLE 1 a) Preparation of Reagent Solutions A, B and C

Reagent Solution A

The moist press cake of the diazonium salt of 1-aminoanthraquinone in sulfuric acid (solids content: 73% by weight) was dissolved in water to give a 2.5% strength by weight solution. The pH of the solution was about 1.2.

Reagent Solution B

A 0.063 molar diazonium chloride solution was obtained by aqueous diazotization of 2-(3-phenyl-1,2,4-oxadiazol-5-yl)aniline with sodium nitrite. The pH of the solution was about 0.1.

Reagent Solution C

A 0.208 molar diazonium chloride solution was obtained by aqueous diazotization of 2-chloro-4-nitroaniline with sodium nitrite. The pH of the solution was about 0.

b) General Detection Reaction in Acidic Solution

The particular aniline is dissolved in a concentration of 10 ppm in diesel fuel. 10 ml of this solution was shaken thoroughly for 1 minute with 0.1 ml of reagent solution A described above. The mixture was then shaken with 3 ml of 9% strength hydrochloric acid, again for 1 minute. After the phases had settled out, the lower aqueous phase was found to be colored.

For the photometric measurement, the aqueous phase was diluted to 10% of the original concentration with distilled water.

c) General Detection Reaction in Buffered Aqueous Solution 10 g of the diesel fuel marked with 10 ppm were extracted with 1 g of 9% strength by weight hydrochloric acid, the aqueous phase was neutralized with sodium hydroxide solution and in each case four times the amount of one of the three buffer solutions 1, 2 and 3 stated below was added.

Buffer solution 1: 5% strength by weight aqueous citric acid solution, brought to pH 3.3 with 10% weight sodium hydroxide solution.

Buffer solution 2: 5% strength by weight aqueous potassium dihydrogen phosphate solution having a pH of 4.4.

Buffer solution 3: 5% strength by weight aqueous sodium acetate trihydrate solution having a pH of 8.2.

0.1 g of one of the three reagent solutions A, B or C was then added.

The coupling generally takes place very rapidly, but it can in most cases be further accelerated by heating.

The results of the investigations are shown in the Table below. The intensity of the color is assessed by ratings (from 1 to 5) (1: no color, 5: very intense color). It is also stated if the color reaction occurs immediately.

d) Production of the Reagent Paper 5 g of the press cake of the diazonium salt of 1-aminoanthraquinone, stated under reagent solution A, were dissolved in 95 ml of distilled water in an ultrasonic bath, and the solution was filtered over a folded filter. Strips of filter paper were immersed in this solution, the excess solution was removed and the wet strips were stored in the dark in order to dry. When these papers were stored in the dark, there was no reduction in the reactivity even after several weeks, but the diazo paper acquired a brownish discoloration. On storage at 50° C. for 8 days, the discoloration of the paper was considerable but these papers too were still suitable for the color test.

e) Detection by Means of Reagent Paper 1 g of 4% strength by weight of hydrochloric acid was added to 10 ml of fuel oil which was marked with 10 ppm of N,N-[bis(2-hydroxyethyl)]-3-methylaniline (cf. Example 3) in a test tube, and the test tube was shaken vigorously by hand for 1 minute. After phase separation was complete, the lower aqueous phase was used for the subsequent detection experiments.

0.55 ml of 33% strength by weight aqueous sodium acetate trihydrate solution was added to 1 g of this aqueous phase. The pH of this solution was 4.5. One drop of this solution was added to the diazo paper, which immediately exhibited a red color.

Instead of dropwise addition onto the diazo paper, it is also possible to place a strip of this paper in the solution. Here, the dilute aromatic amine solution runs on the diazo paper and develops the dye only at the start since the dye then no longer runs. This spot becomes increasingly intense as a result of the further supply of aniline, and the aniline can therefore be detected satisfactorily even in dilute solutions.

This concentration effect is particularly advantageous when it is intended to detect only traces of aniline in a test on the road.

Alternatively, it is also possible to add scraps of diazo paper to the solution. The diazonium salt dissolves from this and rapidly discolors the amine solution. In some cases, the solution has to be heated.

f) Comparison (Blank Sample)

For comparison, 10 ml of the unmarked diesel fuel were thoroughly shaken for 1 minute with 0.1 ml of reagent solution A. Thereafter, vigorous shaking was carried out again with 3 ml of 9% strength by weight hydrochloric acid. After the phases had settled out, the aqueous phase appeared to be more or less strongly yellowish, depending on the diesel fuel grade. For the photometric evaluation (cf. b)), the aqueous, virtually colorless solution of this blank sample, which solution had been diluted to 10% of the original concentration, was placed in the reference beam.

The detection reaction was also carried out in buffered solution, similarly to c).

EXAMPLE 2 a) The Diazonium hydrogen sulfate of 1-aminoanthraquinone was mixed with titanium dioxide in weight ratio 1:1 and triturated in a mortar.

The powder thus formed was then mixed with an amount of water such that a 0.5% strength by weight solution of the diazonium salt formed. After filtration, the solution was stored in a vessel protected from light.

b) 1 drop (0.05 ml) of the solution described under a), which had been diluted again to half the concentration (1:1) with demineralized water, was added to 10 ml of diesel fuel which had been marked with 10 ppm of N-ethyl-N-(2-hydroxyethyl)-3-methylaniline. The mixture was then shaken for 1 minute. Two phases formed, the lower (aqueous) phase having a substantially bluish red color.

In the case of a blank sample with unmarked diesel fuel, the aqueous phase had virtually no color at all.

The marker is thus detectable in a diesel fuel even in a concentration of 1 ppm.

The detection reaction described here can be used for all anilines of the formula I. The anilines of the formula I can also be quantitatively detected in this way (for example by means of HPLC or photometric determination).

TABLE

| Example No. | Aniline | REAGENT SOLUTION A | | | REAGENT SOLUTION B | | |
|---|---|---|---|---|---|---|---|
| | | Buffer 1 | Buffer 2 | Buffer 3 | Buffer 1 | Buffer 2 | Buffer 3 |
| 1 | 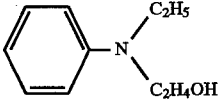 | red | 3 red 3 | orange 3 | 1 | 1 orange | 3 |
| 3 (Comparison) | — | 1 | 1 | 1 | 1 | 1 | 1 |
| 4 | 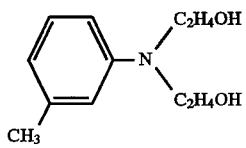 | violet immediately | 5 | 5 | 2 red, cloudy | 3 red 3 | brown 3 |

TABLE-continued
| | | | | | | | | | | | |
|---|---|---|---|---|---|---|---|---|---|---|---|
| 5 | 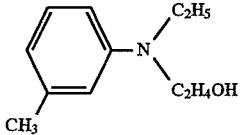 | red rapid | 3 | 2 | brown | 3 | 1 | | 1 | orange | 3 |
| 6 | 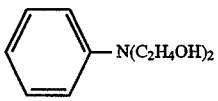 | red | 3 | 1 | yellow | 1 | 2 | | 1 | yellow | 3 |
| 7 | 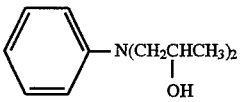 | red | 3 | 1 | | 1 | 2 | | 1 | | 2 |
| 8 | 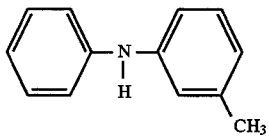 | yellow | 2 | 3 | brown | 3 | yellow | 3 | reddish | 2 | yellowish brown | 3 |
| 9 | 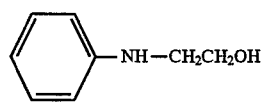 | red | 2 | 1 | | 1 | 2 | | 1 | yellow, cloudy | 2 |
| 10 | 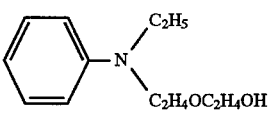 | orange | 2 | 2 | | 2 | yellow | 2 | | 1 | yellow | 3 |
| 11 | 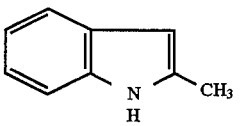 | brown immediately | 2 | 1 | | 1 | yellow | 3 | yellow | 3 | yellow, cloudy | 3 |
| 12 | 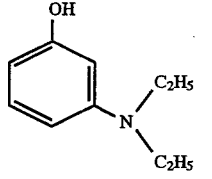 | yellow | 2 | yellow | 3 | yellow | 3 | brown | 3 | brown | 3 | orange | 4 |
| 13 | 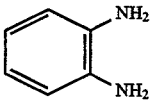 | orange-brown | 2 | 2 | | 2 | | 2 | | 2 | yellow | 3 |
| 14 | 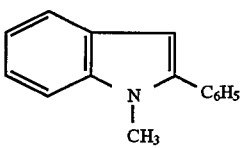 | yellow | 2 | 1 | | 1 | yellow | 3 | yellow | 3 | yellow | 3 |
| 15 | 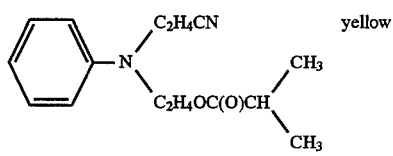 | yellow | 2 | 1 | | 1 | 2 | | 1 | | 2 |

TABLE-continued

| | | | | | | | | | | | | |
|---|---|---|---|---|---|---|---|---|---|---|---|---|
| 16 | 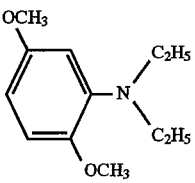 | | 1 | | 1 red | | 3 | | 1 | | 1 | 1 |
| 17 | 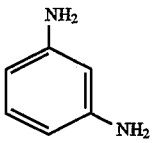 | orange immediately | 4 | orange precipitate | 3 | orange precipitate | 3 | yellow | 4 | yellow | 3 orange precipitate | 5 |
| 18 | 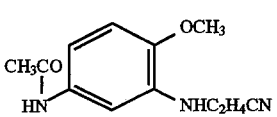 | red | 3 | bluish red | 3 | orange | 2 | red | 4 | red | 4 orange | 3 |
| 19 | 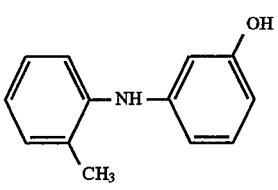 | orange | 5 | orange | 4 | orange | 4 | orange | 3 | orange | 3 orange | 3 |
| 20 | 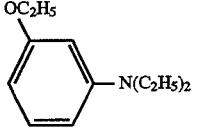 | orange | 3 | orange | 3 | orange | 3 | | 1 | | 1 reddish | 1 |
| 21 | 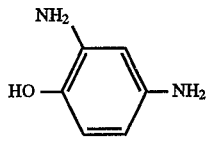 | orange | 4 | | 2 | | 2 | | 2 | | 2 | 2 |
| 22 | 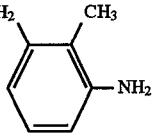 | orange immediately | 5 | orange immediately | 4 | orange immediately | 4 | orange | 4 | orange | 3 orange immediately | 4 |
| 23 | 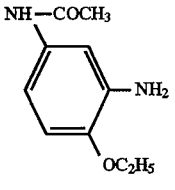 | red immediately | 5 | violet | 5 | brown | 4 | orange | 3 | orange | 3 orange | 4 |
| 24 | 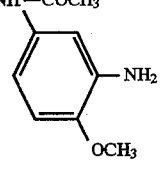 | violet | 5 | violet | 5 | orange | 3 | orange | 3 | | 1 orange | 3 |
| 25 | 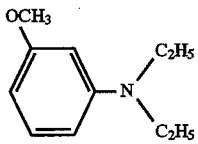 | red | 3 | orange | 4 | orange | 4 | | 1 | | 1 orange | 1 |

TABLE-continued

| # | Structure | Color | | | | | | | | | |
|---|---|---|---|---|---|---|---|---|---|---|---|
| 26 | 3-NHCOCH₃, N(C₂H₄OCOCH₃)₂ aniline | red | 3 | orange | 2 | | 1 | | | | |
| 27 | 2,5-di(OC₄H₉), 3-NH₂ aniline | orange | 3 | orange | 3 | orange | 2 | orange | 2 | orange | 3 orange 3 |
| 28 | 3-CH₃-N,N-diethylaniline | yellow | 2 | | 1 | | 1 | | 1 | | 1 1 |
| 29 | 3-amino-4-hydroxybiphenyl | yellow | 2 | orange | 2 | | 1 | | 1 | | 1 1 |
| 30 | 3-NHCOCH₃, N(CH₂CH₂OH)(CH₂CH₂CN) aniline | yellow | 2 | | | | | | | | |
| 31 | 2-methoxyaniline | yellow | 3 | | 1 | | 3 | | 1 | | 1 yellow 2 |
| 32 | 4-methoxyaniline | yellow | 2 | | 1 | orange | 2 | | 1 | | 1 yellow 2 |
| 33 | 3-NHCOC₂H₅, N(C₂H₅)₂ aniline | yellow | 2 | | 1 | orange | 3 | | 1 | | 1 orange 2 |
| 34 | 3-NHCOCH₃-aniline (with NH₂) | yellow | 2 | | 1 | | 1 | | 1 | | 1 yellow 2 |
| 35 | 3-N(C₂H₅)₂, NHCO(OC₂H₄)₂H aniline | yellow | 2 | | 1 | orange immediately | 3 | | 1 | | 1 orange 2 |
| 36 | 3-NHCONH₂ aniline | yellow | 2 | | 1 | | 1 | | 1 | | 1 yellow 2 |

TABLE-continued

| # | Structure | | | | | | | | | | | |
|---|---|---|---|---|---|---|---|---|---|---|---|---|
| 37 | 3-methylaniline (CH₃, NH₂) | yellow | 2 | | 1 | orange | 3 | 1 | | 1 | yellow | 2 |
| 38 | 4-methylaniline (H₂N, CH₃) | yellow | 2 | yellow | 2 | orange | 2 | 1 | | 1 | | 1 |
| 39 | N,N-diethylaniline (C₂H₅, C₂H₅) | yellow | 2 | | 1 | | 1 | 1 | | 1 | | 1 |
| 40 | 4-methyl-N,N-dimethylaniline (H₃C, CH₃, CH₃) | orange | 2 | | 1 | | | 1 | | 1 | | 1 |
| 41 | NH—COCH₃, N(C₂H₅)₂ | red | 2 | red | 3 | red | 4 | 1 | | 1 | orange | 3 |
| 42 | NH—COCH₃, N(C₂H₅)₂, OCH₃ | yellow | 2 | | | | | | | | | |
| 43 | NH—COCH₃, N(C₂H₄OCOCH₃)₂, OCH₃ | yellow | 2 | | | | | | | | | |
| 44 | CH₃O, NH₂ | | 2 | | 2 | | 2 | orange | 3 | orange | 4 | 1 |
| 45 | CH₃, NH₂, OC₂H₅ | orange-red | 4 | orange | 3 | orange | 3 | orange | 4 | orange | 4 | orange | 3 |
| 46 | phenyl-NH-phenyl-OCH₃ | red | 4 | red | 3 | | 1 | orange | 4 | orange | 3 | orange | 2 |
| 47 | OH, morpholine | orange | 3 | | 2 | | 2 | | 2 | | 2 | orange | 3 |

TABLE-continued

| | | | | | | | | | | |
|---|---|---|---|---|---|---|---|---|---|---|
| 48 | 3-CH₃-C₆H₄-NH-C₂H₄OC₆H₅ | red | 3 | reddish orange | 2 | orange | 2 | 2 orange | 3 orange | 3 |
| 49 | 2-CH₃-C₆H₄-NH-C₂H₄OH | orange | 3 | orange | 2 | | 1 | 1 orange | 2 orange | 3 |

| Example No. | Aniline | REAGENT SOLUTION C | | | | | |
|---|---|---|---|---|---|---|---|
| | | Buffer 1 | | Buffer 2 | | Buffer 3 | |
| 1 | C₆H₅-N(C₂H₅)(C₂H₄OH) | | 2 | orange-red | 3 | yellow | 2 |
| 3 (Comparison) | — | yellow | 2 | yellow | 2 | yellow | 2 |
| 4 | 3-CH₃-C₆H₄-N(C₂H₄OH)₂ | orange | 4 | orange | 4 | orange | 4 |
| 5 | 3-CH₃-C₆H₄-N(C₂H₅)(C₂H₄OH) | orange | 4 | orange | 4 | orange | 5 |
| 6 | C₆H₅-N(C₂H₄OH)₂ | orange | 4 | orange | 3 | orange | 5 |
| 7 | C₆H₅-N(CH₂CHCH₃)₂-OH | orange | 4 | orange | 4 | orange | 4 |
| 8 | C₆H₅-NH-C₆H₄-3-CH₃ | yellow | 3 | orange | 4 | orange | 4 |
| 9 | C₆H₅-NH-CH₂CH₂OH | yellow | 3 | yellow | 3 | yellow | 3 |
| 10 | C₆H₅-N(C₂H₅)(C₂H₄OC₂H₄OH) | yellow | 3 | yellow | 3 | orange | 4 |
| 11 | 2-methylindole | yellow precipitate | 3 | yellow precipitate | 3 | yellow, cloudy | 3 |

TABLE-continued

| | | | | | | | |
|---|---|---|---|---|---|---|---|
| 12 | 3-(N,N-diethylamino)phenol | orange | 5 | orange | 5 | orange | 5 |
| 13 | 1,2-diaminobenzene | orange | 4 | orange | 4 | orange | 4 |
| 14 | 1-methyl-2-phenylindole | yellow | 3 | yellow | 3 | yellow | 3 |
| 15 | N-(2-cyanoethyl)-N-(2-isobutyroyloxyethyl)aniline | yellow | 4 | yellow | 4 | yellow | 5 |
| 16 | 2,5-dimethoxy-N,N-diethylaniline | yellow | 3 | yellow | 3 | orange | 4 |
| 17 | 1,3-diaminobenzene | orange precipitate | 4 | orange precipitate | 3 | orange precipitate | 4 |
| 18 | N-acetyl-N'-(2-cyanoethyl)-4-methoxy-1,3-phenylenediamine | orange | 4 | orange | 4 | orange | 4 |
| 19 | 2-methyl-2'-hydroxy-diphenylamine | | | | | | |
| 20 | 3-ethoxy-N,N-diethylaniline | | | | | | |
| 21 | 2-amino-4-aminophenol | | | | | | |

TABLE-continued

| # | Structure |
|---|---|
| 22 | 2,6-diamino-3-methylbenzene (NH₂, CH₃, NH₂ on benzene) |
| 23 | 5-acetamido-2-ethoxyaniline (NH—COCH₃, NH₂, OC₂H₅) |
| 24 | 5-acetamido-2-methoxyaniline (NH—COCH₃, NH₂, OCH₃) |
| 25 | 3-methoxy-N,N-diethylaniline (OCH₃, N(C₂H₅)₂) |
| 26 | 3-acetamido-N,N-bis(2-acetoxyethyl)aniline (NH—COCH₃, N(C₂H₄OCOCH₃)₂) |
| 27 | 2,5-dibutoxyaniline (OC₄H₉, NH₂, OC₄H₉) |
| 28 | 3-methyl-N,N-diethylaniline (CH₃, N(C₂H₅)₂) |
| 29 | 3-amino-4-hydroxybiphenyl (NH₂, OH on biphenyl) |
| 30 | 3-acetamido-N-(2-hydroxyethyl)-N-(2-cyanoethyl)aniline (NH—COCH₃, N(CH₂CH₂OH)(CH₂CH₂CN)) |
| 31 | 2-methoxyaniline (OCH₃, NH₂) |

TABLE-continued
| | |
|---|---|
| 32 | 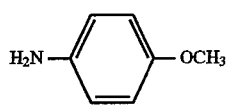 |
| 33 | 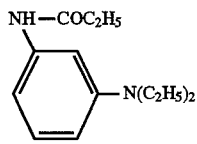 |
| 34 | 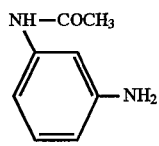 |
| 35 | 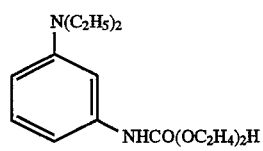 |
| 36 | 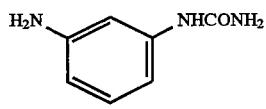 |
| 37 | 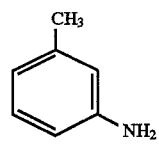 |
| 38 | 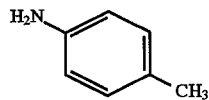 |
| 39 | 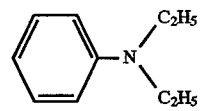 |
| 40 | 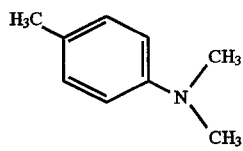 |
| 41 | 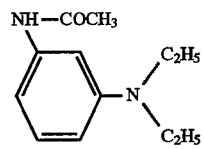 |
| 42 | 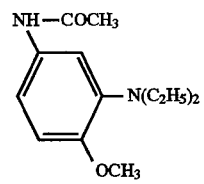 |

TABLE-continued

| 43 | 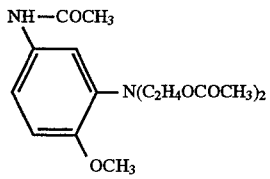 |
|---|---|

Further advantageous diazonium compounds are, for example, substances shown below

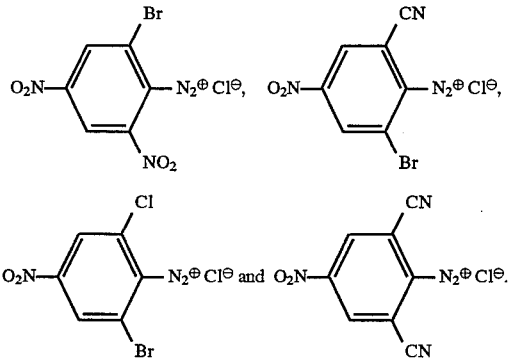

On coupling with the anilines of the formulae

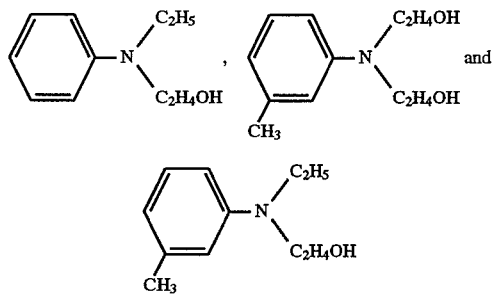

which are used as markers, they each give a blue color reaction.

We claim:

1. A method of marking mineral oils, comprising:
mixing, into a mineral oil, a marker aniline compound of formula I:

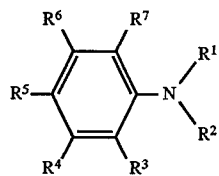

where $R^1$ and $R^2$ independently of one another are each hydrogen, $C_1-C_{18}$-alkyl which is unsubstituted or substituted and may be interrupted by 1 to 3 oxygen atoms as ether functional groups or from 1 to 3 $C_1-C_4$-alkylimino groups, or $C_3-C_{18}$-alkenyl or unsubstituted or substituted phenyl, or $R^1$ and $R^2$, together with the nitrogen atom which links them, may be a 5-membered or 6-membered saturated heterocyclic radical which may have a further hetero atom, or $R^1$ may furthermore be a radical of the formula $OL^1$ or $NL^1L^2$, where $L^1$ and $L^2$ independently of one another are each hydrogen, unsubstituted or substituted $C_1-C_{18}$-alkyl, $C_3-C_{18}$-alkenyl or unsubstituted or substituted phenyl, $R^3$ and $R^7$ independently of one another are each hydrogen, unsubstituted or substituted $C_1-C_{18}$-alkyl, $C_2-C_{18}$-alkenyl, cyano, nitro, formyl, unsubstituted or substituted $C_2-C_4$-alkanoyl, formylamino, unsubstituted or substituted $C_2-C_4$-alkanoylamino, benzoylamino or a radical of the formula $OL^1$, $CH_2COOL^1$, $NL^1L^2$, $SL^1$ or $SO_2NL^1L^2$, where $L^1$ and $L^2$ each have the above-mentioned meanings, or together with $R^2$ are $C_2$- or $C_3$-alkylene which is unsubstituted or monosubstituted to trisubstituted by methyl or are unsubstituted or phenyl-substituted $C_2$- or $C_3$-alkenylene, $R^4$ is hydrogen, unsubstituted or substituted $C_1-C_{18}$-alkyl, $C_2-C_{18}$-alkenyl, nitro or a radical of the formula $OL^1$, $NL^1L^2$, $COOL^1$ or $SO_2L^1L^2$, where $L^1$ and $L^2$ each have the above-mentioned meanings, and $R^5$ and $R^6$ independently of one another are each hydrogen, unsubstituted or substituted $C_1-C_{18}$-alkyl, $C_2-C_{18}$-alkenyl, unsubstituted or substituted phenyl, nitro, formylamino, unsubstituted or substituted $C_2-C_4$-alkanoylamino, benzoylamino or a radical of the formula $OL^1$, $NL^1L^2$, $SO_2NL^1L^2$, $SO_2L^3$, $COL^1$ or $COOL^1$, where $L^1$ and $L^2$ each have the above-mentioned meanings and $L^3$ is unsubstituted or substituted $C_1-C_{18}$-alkyl, $C_3-C_{18}$-alkenyl or unsubstituted or substituted phenyl, with the proviso that at least one of $R^3$, $R^5$ or $R^7$ is hydrogen and with the proviso that aniline and all toluidine isomers are excluded.

2. The method of claim 1, wherein $R^1$ and $R^2$ independently of one another are each hydrogen, $C_1-C_{15}$-alkyl, which is unsubstituted or substituted and which may be interrupted by 1 to 3 oxygen atoms as ether functional groups, or from 1 to 3 $C_{1-4}$alkylimino groups, or allyl or unsubstituted or substituted phenyl, or $R^1$ and $R^2$ together with the nitrogen atom linking them are a 5-membered or 6-membered saturated heterocyclic radical which may have a further hetero atom, $R^3$ and $R^7$ independently of one another are each hydrogen, or $C_{1-4}$-alkoxy or, together with $R^2$, are 1,3-propylene which is unsubstituted or monosubstituted to trisubstituted by methyl, $R^4$ and $R^5$ are each hydrogen and $R^6$ is hydrogen, $C_{1-4}$-alkyl, $C_{1-4}$-alkoxy, $C_{1-4}$-alkanoylamino or benzoylamino.

3. The method of claim 1, wherein $R^1$ and $R^2$ are each hydrogen or $C_{1-4}$-alkyl or at least one of $R^1$ and $R^2$ is $C_{2-15}$-alkyl which is substituted by hydroxyl and may be interrupted by from 1 to 3 oxygen atoms as ether functional group(s) or from 1 to 3 $C_{1-4}$-alkylimino groups, and $R^6$ is $C_{1-4}$-alkyl.

4. A mineral oil containing at least one marker aniline compound of formula I:

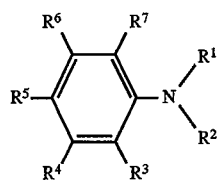

(I)

where

R$^1$ and R$^2$ independently of one another are each hydrogen, C$_1$–C$_{18}$-alkyl which is unsubstituted or substituted and may be interrupted by 1 to 3 oxygen atoms as ether functional groups or from 1 to 3 C$_1$–C$_4$-alkylimino groups, or C$_3$–C$_{18}$-alkenyl or unsubstituted or substituted phenyl, or R$^1$ and R$^2$, together with the nitrogen atom which links them, may be a 5-membered or 6-membered saturated heterocyclic radical which may have a further hetero atom, or R$^1$ may furthermore be a radical of the formula OL$^1$ or NL$^1$L$^2$, where L$^1$ and L$^2$ independently of one another are each hydrogen, unsubstituted or substituted C$_1$–C$_{18}$-alkyl, C$_3$–C$_{18}$-alkenyl or unsubstituted or substituted phenyl, R$^3$ and R$^7$ independently of one another are each hydrogen, unsubstituted or substituted C$_1$–C$_{18}$-alkyl, C$_2$–C$_{18}$-alkenyl, cyano, nitro, formyl, unsubstituted or substituted C$_2$–C$_4$-alkanoyl, formylamino, unsubstituted or substituted C$_2$–C$_4$-alkanoylamino, benzoylamino or a radical of the formula OL$^1$, CH$_2$COOL$^1$, NL$^1$L$^2$, SL$^1$ or SO$_2$NL$^1$L$^2$, where L$^1$ and L$^2$ each have the above-mentioned meanings, or together with R$^2$ are C$_2$- or C$_3$-alkylene which is unsubstituted or monosubstituted to trisubstituted by methyl or are unsubstituted or phenyl-substituted C$_2$- or C$_3$-alkenylene, R$^4$ is hydrogen, unsubstituted or substituted C$_1$–C$_{18}$-alkyl, C$_2$–C$_{18}$-alkenyl, nitro or a radical of the formula OL$^1$, NL$^1$L$^2$, COOL$^1$ or SO$_2$L$^1$L$^2$, where L$^1$ and L$^2$ each have the above-mentioned meanings, and R$^5$ and R$^6$ independently of one another are each hydrogen, unsubstituted or substituted C$_1$–C$_{18}$-alkyl, C$_2$–C$_{18}$-alkenyl, unsubstituted or substituted phenyl, nitro, formylamino, unsubstituted or substituted C$_2$–C$_4$-alkanoylamino, benzoylamino or a radical of the formula OL$^i$, NL$^1$L$^2$, SO$_2$NL$^1$L$^2$, SO$_2$L$^3$, COL$^1$ or COOL$^1$, where L$^1$ and L$^2$ each have the above-mentioned meanings and L$^3$ is unsubstituted or substituted C$_1$–C$_{18}$-alkyl, C$_3$–C$_{18}$-alkenyl or unsubstituted or substituted phenyl, with the proviso that at least one of R$^3$, R$^5$ or R$^7$ is hydrogen, and with the proviso that aniline and all toluidine isomers are excluded.

5. A method, for detecting the presence of at least one marker aniline compound of the marker containing mineral oil of claim 4, comprising:

extracting the at least one marker aniline compound from the mineral oil with an acidic aqueous solution containing a diazonium salt, wherein the diazonium salt is derived from an amine selected from the group consisting of aminoanthraquinone, aminonaphthalene, aniline, aminothiophene, aminothiazole and aminobenzoisothiazole; and then detecting the presence of said at least one marker aniline compound by the development of color in an aqueous phase which forms.

6. A method for detecting the presence of at least one marker aniline compound of the marker containing mineral oil of claim 4, comprising:

extracting the at least one marker aniline compound from the mineral oil with an aqueous acid solution thereby forming an aqueous phase containing extracted marker aniline compound;

neutralizing the aqueous phase obtained with a basic aqueous solution; and detecting the presence of said at least one marker aniline compound in the aqueous phase by adding an aqueous solution containing diazonium salt of an amine selected from the group consisting of aminoanthraquinone, aminonaphthalene, aniline, aminothiophene, aminothiazole and aminobenzoisothiazole, to the aqueous phase thereby resulting in the development of color in the aqueous phase.

7. The method of claim 6, wherein, after the aqueous extract phase is neutralized, the aqueous phase is buffered before treatment with diazonium salt.

8. A method for detecting the presence of at least one marker aniline compound of the marker containing mineral oil of claim 4, comprising:

extracting the at least one marker aniline compound from the mineral oil with an aqueous solution thereby forming an aqueous phase containing extracted marker aniline compound; and detecting the presence of said at least one marker aniline compound by contacting the aqueous phase with a solid substrate impregnated with a diazonium salt derived from an amine selected from the group consisting of aminoanthraquinone, aminonaphthalene, aniline, aminothiophene, aminothiazole and aminobenzoisothiazole, thereby forming a colored azo dye in the solid substrate.

9. The method of claim 8, wherein the aqueous phase containing said at least one marker aniline compound is buffered.

* * * * *